(12) United States Patent
Burris et al.

(10) Patent No.: US 6,238,087 B1
(45) Date of Patent: May 29, 2001

(54) METHOD AND APPARATUS FOR CHARACTERIZING A QUENCH

(75) Inventors: Kenneth W. Burris, Peoria; Leonid Chuzhoy, Dunlap; Thomas E. Clements, Peoria, all of IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 09/351,817

(22) Filed: Jul. 13, 1999

(51) Int. Cl.$^7$ .................................................. G01N 25/00
(52) U.S. Cl. .............................. 374/43; 374/44; 374/45; 374/145
(58) Field of Search ....................... 374/43–45, 57, 374/28–30, 145

(56) References Cited

U.S. PATENT DOCUMENTS

| | | | |
|---|---|---|---|
| 4,412,752 | 11/1983 | Cellitti et al. ................ | 374/43 |
| 4,563,097 | * 1/1986 | Katafuchi ...................... | 374/43 |
| 4,618,269 | * 10/1986 | Badrak et al. ................. | 384/95 |
| 4,636,089 | * 1/1987 | Schumann ..................... | 374/45 |
| 4,722,611 | * 2/1988 | Hultgen ........................ | 374/43 |
| 4,978,230 | * 12/1990 | Adiutori et al. .............. | 374/43 |
| 5,178,463 | * 1/1993 | Berry, Jr. et al. ............. | 374/43 |
| 5,196,075 | * 3/1993 | Jansen et al. ................. | 148/530 |
| 5,224,775 | * 7/1993 | Readings et al. ............. | 374/11 |
| 5,374,322 | * 12/1994 | Okada et al. .................. | 148/663 |
| 5,601,363 | 2/1997 | Keil et al. ..................... | 374/45 |
| 5,722,772 | 3/1998 | Keil et al. ..................... | 374/45 |
| 5,820,705 | * 10/1998 | Yu et al. ........................ | 148/633 |
| 5,918,473 | * 7/1999 | Gendron et al. .............. | 62/129 |
| 6,099,162 | * 8/2000 | Walsh ............................ | 374/30 |

FOREIGN PATENT DOCUMENTS 52-064987 * 5/1977 (JP).

* cited by examiner

Primary Examiner—G. Bradley Bennett
Assistant Examiner—Gail Verbitsky
(74) Attorney, Agent, or Firm—John W. Morrison

(57) ABSTRACT

A method and apparatus for characterizing a quench for producing desired hardness characteristics on a steel part. The characterization preferably includes a series of heat transfer coefficients versus temperature for the quench determined from information representative of known quenches and distinguishing part characteristics such as geometry, size and composition. The quench characterization determined using the present method and apparatus can be utilized in hardness prediction software programs, and for determining a suitable quench for producing the desired hardness characteristics on the part.

15 Claims, 5 Drawing Sheets

METHOD AND APPARATUS FOR CHARACTERIZING A QUENCH

TECHNICAL FIELD

This invention relates generally to heat treating and more particularly, to a method and apparatus for determining a series of heat transfer coefficients for characterizing a quench for purposes such as use in computer programs for predicting hardness characteristics of a steel part subject to the quench, and for selecting a quench for producing desired hardness characteristics on a part.

BACKGROUND ART

Heat treatment for hardening a steel part involves heating the part to a high temperature, typically to reach the austenite condition, then subjecting the part to a quench which rapidly cools the part for achieving desired hardness characteristics on at least the outer surface of the part, and in many cases, also at one or more internal locations between the outer surface and the core of the part. Numerous fluid mediums are commonly used for quenching, a particular quench typically being selected based on experience and various factors including the hardness characteristics one is trying to achieve, and size, shape and composition of the part to be quenched. Examples of commonly used quench mediums include water, oil, aqueous polymer solutions and mixtures of the above mediums. Air blasts can also be used. Additionally, liquid quench mediums can be in a still state or in varying degrees of agitation. Other factors observed to affect characteristics of a particular quench include level of impurities in the quench medium, volume of the quench medium, tank size, pump flow rates (for agitation), and the like.

Currently, a variety of methods for determining hardenability of steels are known. Reference for instance, the well known Jominy End Quench Test. The Jominy End Quench Test involves quenching one end of a cylindrical steel specimen with a water quench, measuring the hardness of the specimen at one-sixteenth inch increments from the quenched end, then preparing a plot of the hardness measurements versus distance from the quenched end. The Jominy test is specifically done with a water quench and only quenches the flat, blunt end of the specimen, to produce uniaxial heat flow through the specimen. The test holds the specimen shape and size and the quench medium constant, so that hardenability of various tested steel compositions can be determined and compared. However, since the Jominy test utilizes only a water end quench, which provides only uniaxial heat flow, it has been found to be less than an ideal tool for predicting hardness of actual parts having shapes and/or sizes that differ substantially from the test specimens. The Jominy test is also less than an ideal tool when a different quench is used, for instance, wherein a different quench medium is used, and wherein most of a part, or an entire part, is quenched instead of just the end.

It is also known to determine hardness of steel parts experimentally, by actually making a sample part and subjecting the part to a desired quench. Then, hardness measurements are taken at a desired location or locations on the part to determine whether the quench achieved the desired hardness characteristics. For this determination, the part can be sectioned at one or more locations of interest and the hardness measured on a sectional surface or surfaces to ascertain hardness at internal locations on the part. However, this can be an expensive and time consuming process, depending on factors such as the complexity of the part, and the number of experiments required to determine a quench which produces the desired hardness characteristics.

Other tools for predicting hardness of steel parts of different shapes and sizes include the various well known commercially available hardness prediction software programs such as the HEARTS program available from CRC Research Institute, Inc. of Santa Clara, Calif. Programs such as the HEARTS program are operable using finite element analysis or similar techniques for predicting a hardness traverse for a part when provided with certain predetermined inputs including chemistry of the part, dimensions of the part, geometric characteristics of the part and a characterization of a particular quench to be used, which characterization is typically a series of convection heat transfer coefficients for the quench.

A limitation of the known hardness prediction programs, however, is that the accuracy of the hardness traverse output has been found to be only as good as the accuracy of the inputted information. In particular, it has been found that an outputted hardness traverse is significantly negatively affected by inaccurate heat transfer coefficient inputs. This is problematic because only limited reliable heat transfer coefficient data is available, necessitating in many instances the use of known data for one kind of quench for determining hardness produced by different quenches, and the use of estimates, which are accurate only within the capabilities of the estimator.

It is also known to determine heat transfer coefficients for a quench experimentally. In this regard, it is known that the hardness of a part at a particular location is a function of the cooling rate at that location, which in turn is a function of the heat transfer coefficient at the interface between the surface of the part and the quench medium, which heat transfer coefficient fluctuates with temperature. By placing thermocouples at desired locations in a part, measurements of the rate of temperature decline at the locations can be taken over time using well known formulas. This data can then be used to calculate a series of heat transfer coefficients for the quench versus time. The series of heat transfer coefficients can then be inputted into the HEARTS program along with the other inputs discussed above, and a reasonably accurate predicted hardness traverse outputted.

However, collecting temperature data in the above-described manner is time consuming and expensive. Also, it is not uncommon to experience equipment failure such as a thermocouple being destroyed or broken loose due to the initial high temperatures involved, the sudden temperature drop experienced during the quench, handling, and other causes.

Therefore, what is required is a tool which enables more easily determining heat transfer coefficients for characterizing a quench for use in predicting desired hardness characteristics produced on a part subject to the quench, and for determining whether a particular quench will produce desired hardness characteristics on a part, without requiring actually quenching the part and the attendant problems just discussed.

Accordingly, the present invention is directed to overcoming one or more of the problems as set forth above.

DISCLOSURE OF THE INVENTION

In one aspect of the present invention, a method is disclosed for characterizing a quench for producing a desired hardness characteristic on a subject part, the subject part having at least one distinguishing characteristic effecting the hardness characteristic, the method comprising the step of: determining a difference between information representative of the desired hardness characteristic and information representative of a hardness characteristic produced by a known quench on at least one specimen part having the at least one distinguishing characteristic; and if the difference is less than a predetermined value, then producing information representative of a characterization of the known quench; and if the difference is greater than or equal to the predetermined value, then determining and producing information representative of a characterization of a new quench based on the difference.

According to a preferred aspect of the present invention, the quench characterizations are each a series of heat transfer coefficients for the respective quenches. The preferred distinguishing characteristics of the subject part and the specimen parts include, but are not limited to, geometric configuration, size and composition.

According to another aspect of the present invention, apparatus for characterizing a quench for producing a desired hardness characteristic on a subject part having at least one distinguishing characteristic effecting the hardness characteristic, is disclosed. The apparatus includes a storage device containing information representative of a hardness characteristic produced by at least one known quench on at least one specimen part, information representative of at least one distinguishing characteristic of the at least one specimen part, and information representative of a characterization of the at least one known quench. The apparatus also includes a processor operable for determining a difference between information representative of the desired hardness characteristic and the stored information representative of the hardness characteristic produced by the known quench on the at least one specimen, and; if the difference is less than a predetermined value, then retrieving the stored information representative of the characterization of the known quench; and if the difference is greater than or equal to the predetermined value, then determining information representative of a characterization of a new quench based on the difference.

According to a preferred aspect of the present invention, the apparatus further includes an output device operable for outputting the information representative of the characterizations of the quenches.

According to another preferred aspect of the present invention, the storage device contains information representative of hardness characteristics produced by several quenches on a variety of specimens, along with information representative of the geometry, size and composition of the specimens, and heat transfer coefficient information for the respective quenches.

BEST MODE FOR CARRYING OUT THE INVENTION

Figure 1:
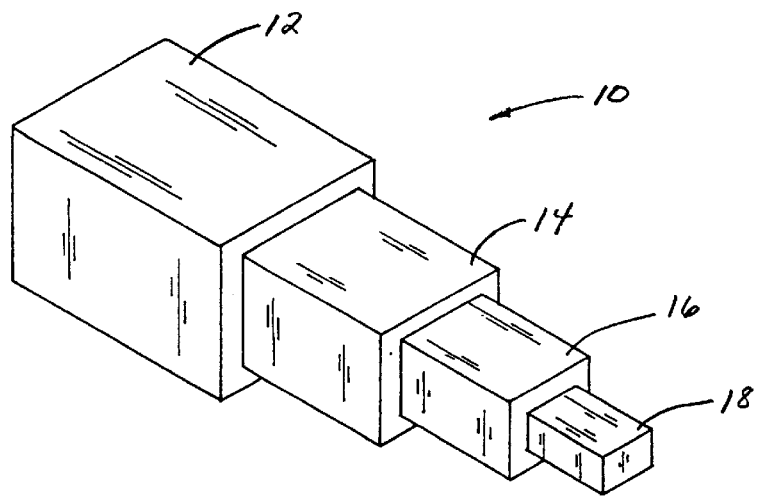
FIG. 1 is a perspective view of a specimen for the present invention, including a plurality of rectangular cross-sectional areas.

The present invention relates to a method and apparatus for characterizing quenches for producing desired hardness characteristics on a wide variety of steel parts. For this invention, hardness data for at least one steel specimen subject to a quench is compiled in a database stored in a suitable storage device, such as a conventional computer memory or the like. The hardness data can include known hardness value traverses taken from handbooks and the like. The hardness data can also be actual hardness measurements taken from specimens or actual parts that have been quenched, either specifically for compiling the present database, or during the course of other research or production activities. In this regard, it is contemplated that the subject database can be as large or as small as required for characterizing quenches anticipated to be used for a particular application.

Factors found to have the greatest impact on the outcome of a quench include the quench medium selected, and distinguishing characteristics of a part or specimen subject to the quench, such as, but not limited to, part geometry and part size, particularly sectional dimensions for solid parts and wall thickness dimensions for hollow parts. The steel composition of the part to be quenched is also a factor, but more generally so, it having been found that generally categorizing steels as low hardenability, medium hardenability and high hardenability is sufficient for the purposes of the present invention. Here, it should be noted that although usable, hardness data from the Jominy End Quench Test is less preferred for use in the present invention because the only variant is composition, which, as explained above, is not as important a factor as the other factors. Also, most actual quenches involve quenching all or most of a part thereby producing multi-directional heat flow through the part, not just uniaxial heat flow as in the Jominy test, which makes the Jominy hardness data less representative of hardness conditions that can be expected when more than just the end of a part is quenched. Here it should also be noted that regardless of whether a part is subject to a quench producing uniaxial heat flow such as the Jominy End Quench Test or multi-directional heat flow such as wherein at least a substantial portion of the part is quenched, hardness at a particular location within the part is a function of the rate of cooling of the part at the location, which in turn is a function of heat transfer from the part at the interface or interfaces between the surface or surfaces of the part and the quench medium, which can be represented mathematically by a coefficient of heat transfer. Further, the coefficient of heat transfer at the interface between the quench medium and the part surface or surfaces will vary with temperature. Thus, if an accurate series of heat transfer coefficients can be determined for a range of temperatures present during the quench, the heat transfer coefficients will serve as an accurate characterization of the quench.

One way to determine the heat transfer coefficients for a quench is to use a simple one dimensional axi-symmetric model representative of a quenched part or specimen. The model includes a plurality of elements extending in a linear arrangement from a surface of the specimen in contact with the quench medium inwardly to a center line of the specimen, with the heat flow or heat flux assumed to be directed outwardly from the part along a line or axis extending through the elements. Importantly, each element will exhibit a specific heat flux rate or cooling rate history during the quench. In steels, this cooling rate history has been found to correlate to hardness for the element. This is important because by having a hardness traverse for a specimen including hardness values that can be correlated to the elements of the model of the specimen, a resultant axi-symmetric model with specific cooling histories for the elements thereof is present. This axi-symmetric model can be analyzed using a suitable conventional modeling technique such as finite element methods or control volume element analysis using the known equation of state:

$$\rho * C_p * \delta T/\delta t = -k^{\delta+hu} \, 2T/\delta x + hu \, 2$$

with $$\dot{q}_x = k^{\delta} T/\delta x = h_c (T - T_i)$$

as boundary conditions, wherein

"$C_p$" specific heat which varies with time and whether the steel is in a 100% pearlite/ferrite structure, a 100% martensite structure, or a mixed micro structure, values for specific heat being readily available from conventional handbooks;

"$\rho$" is density, which for steel is a known constant;

"k" is the thermal conductivity and is also a constant value obtainable from a conventional handbook;

"T" is temperature;

"t" is time;

"$h_c$" is coefficient of heat transfer; and

"x" is distance.

Using the finite element methods or control volume element analysis, the equation of state is solved for the heat transfer coefficient $h_c$ at desired temperatures of the quench to yield a $h_c$ versus temperature curve for the quench. The heat transfer coefficient versus temperature data can then be used as inputs in a hardness prediction program such as the HEARTS program discussed above.

More importantly, for the purposes of the present invention, the above-described modeling and analysis can be used to determine heat transfer coefficients for quenches for parts or specimens having a wide variety of different geometric configurations, sizes and compositions, information representative of which can be stored in the database. In this regard, an important aspect of the finite element methods and control volume element analysis is the ability to alter one or more of the distinguishing characteristics of a modeled part or specimen for determining resultant changes in the heat transfer characteristics of a quench for the part resultant from the varied characteristic or characteristics. Thus, for some parts or specimens, reliable heat transfer coefficient data can be determined by altering parameters in an existing model, without requiring actual quenching and temperature data collection.

As a theoretical example, heat transfer coefficient versus temperature data for a variety of steel specimens of different steel compositions and having different geometric configuration and sizes representative of the materials, geometric configurations and sizes of parts anticipated to be used by a typical manufacturer or heat treat shop, can be compiled.

Here it should be understood that although the specimens can be made from any steel that can be quenched, for the example, the preferred types of steel used are limited to SAE 1040 (a low hardenability steel), SAE 4140 (a medium hardenability steel), and SAE 4340 (a high hardenability steel). These steels are selected because they represent steels commonly used throughout a wide variety of industries. Also, while specimens having various geometric configurations could be used, specimens having cylindrical shapes, rectangular shapes, and half tube shapes as shown in FIGS. 1, 2, 3, and 4, are used, with all of the shapes having a known size or wall thickness (including length and area). These shapes are preferred as they are representative of generic shapes found in various parts used in a wide variety of industries, including shafts, rods, bars, bushings and gears. Finally, while specimens having various wall thicknesses and cross-sectional sizes could be used, the specimens selected for the example have sizes and wall thicknesses of two inches or less. Again, as with geometric configurations, this size limitation is based on part sizes commonly used in a variety of industries.

For the example, five of each of the specimens 10, 20 and 40 are prepared from each of the three selected materials (SAE 1040 Steel, SAE 4140 Steel and SAE 4340 steel) for a total of forty-five (45) specimens. The specimens are first austenized preferably to at least 750° C. Next, at least a substantial portion of each specimen, preferably the entire specimen, is quenched in a medium of interest. Here, five (5) quenches are used, including a highly agitated water quench; a highly agitated oil quench; a less agitated oil quench; a hot oil quench; and a high viscosity air blast quench. Nine (9) specimens, one each of the specimens 10, 20 and 40 of each of the three materials, is subject to each quench. After the quench, the steel specimens are cut or sectioned so that hardness measurements can be taken on the sectional surface from the outer surface inward to the core at predetermined incremental locations along the sectional surface. The cut or section can be made either widthwise or lengthwise, the key being that the core of the specimen is exposed so that the internal hardness measurements can be collected. When collecting the hardness measurements, it is preferable to use either ¹⁄₁₆-inch increments or 1-millimeter (mm) increments, although either larger or smaller increments can be used. Another option is to place a grid on the sectional surface of the specimen and mark each location on the grid where a hardness measurement should be taken. Although any hardness measuring means can be used, it is preferable to use a widely known and commercially available Rockwell Indentations Hardness Test Machine to make the indentations and take the hardness measurements. These results are then tabulated and stored in the database along with the distinguishing characteristics of the specimens, including composition, geometric configuration, and size.

Here it should be recognized that in some instances a quench can be alternatively characterized using only one steel specimen. For example, if a severe quench medium, such as water, is being used, the specimen can be prepared from steel having a low hardenability such as SAE 1040. This is because it has been found that low hardenability steel in a severe quench produces a steeper hardness gradient than high hardenability steel in a severe quench and yields a larger range of hardness data. Therefore a more optimized heat transfer curve can be developed using the low hardenability steel specimen. In contrast, if a severe quench is used and the specimen is composed of a high hardenability steel such as SAE 4340, it has been found that the data will yield a flatter hardness gradient. Someone knowledgeable in the field would be able to choose the steel specimen which best represents the part of interest. For example, the user could choose a steel specimen from either a high hardenability steel, a medium hardenability steel, or a low hardenability steel, to give the hardness measurements of interest. A mild quench can be characterized using a single specimen of high hardenability steel (SAE 4340).

Figure 2:
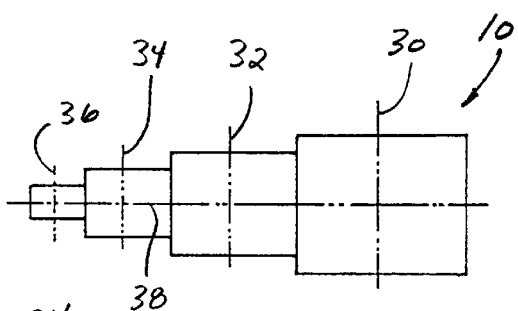
FIG. 2 is a side view of the specimen depicted in FIG. 1, indicating various places where the specimen can be sectioned.
Figure 3:
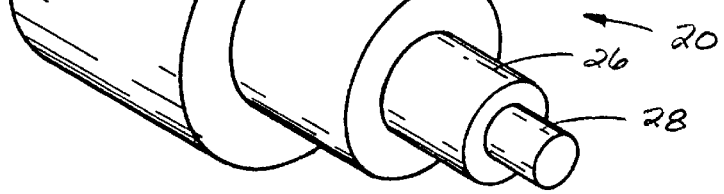
FIG. 3 is a perspective view of another specimen for the present invention, including a plurality of cylindrical cross-sectional areas.

Referring to FIGS. 1 and 2, specimen 10 is shown having four (4) rectangular cross-section portions 12, 14, 16, and 18 of different sizes. Similarly, FIG. 3 depicts specimen 20 having four (4) cylindrical diameters 22, 24, 26, and 28. Sectioning either or both of the specimens 10 and 20 enables the collection of hardness data for all or desired portions of the sectional surfaces. For example, as FIG. 2 indicates, the specimen 10 having different rectangular cross-sectional areas can be cut or sectioned along lines 30, 32, 34, and 36 to create sectional surfaces extending from the outer surface inward to the core on each sectioned piece of the specimen. This enables collecting hardness data for four (4) different size rectangles while only having to quench one specimen. Rather than make four (4) width wise cuts, a single lengthwise cut or section 38 can be made and hardness measurements taken on the sectional surface from the outer surface inward to the core at each of the four (4) cross-sectional areas 12, 14, 16 and 18. Similarly, for the cylindrical specimen 20 shown in FIG. 3, cuts or sections could be made on the quenched specimen 20 at each of the diameters 22, 24 and 26, or a single longitudinally extending section could be made.

Figure 4:
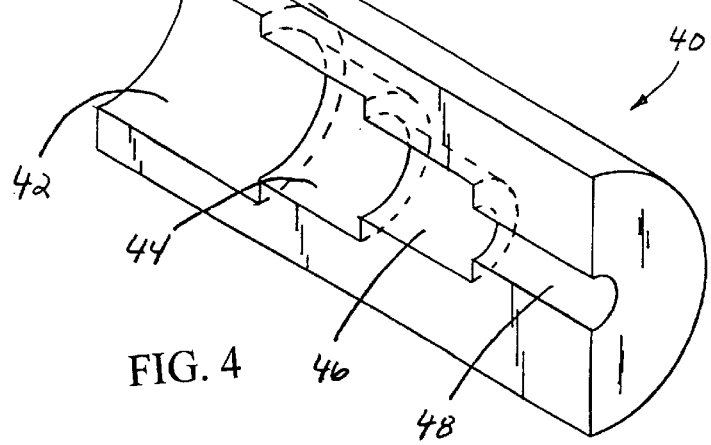
FIG. 4 is a perspective view of still another specimen for the present invention, including a half tube shape indicating a half opening throughout the length of the half tube, with the half tube having a plurality of inner wall thicknesses.

A quench can have different effects on the outside and inside of a hollow part. Therefore, when dealing with hollow parts it is important to know the effect of a quench on both the outside of the hollow part and the inside of the hollow part. The half tube specimen 40 as depicted in FIG. 4 is used for those situations. As with the specimens 10 and 20 depicted in FIGS. 1 and 3, the half tube specimen 40 also can be cut or sectioned widthwise at each diameter or lengthwise. Hardness data can then be collected along the sectional surface for each diameter 42, 44, 46 and 48, both from the inner surface to the core of the section and from the outer surface to the core of the section. Thus, for the 45 specimens, 240 hardness traverses are obtained.

To determine heat transfer curve coefficients for each of the quenches, thermocouples can be placed in desired specimens, and the heat transfer data calculated in the above described manner using the equation of state. Alternatively, an initial heat transfer coefficient curve for each of the five (5) quenches can be determined. Then, information representative of the heat transfer values from the curves can be inputted into a commercial hardness predication program, such as the HEARTS program discussed above, along with the distinguishing characteristics of the particular specimens, to determine theoretical hardness characteristics for the specimens. The theoretical hardness characteristics can then be compared with the actual hardness characteristics measured above, to determine factors representative of the correlation between the distinguishing characteristics of a part (geometry, size, composition), hardness, and the heat transfer coefficients.

Figure 5:
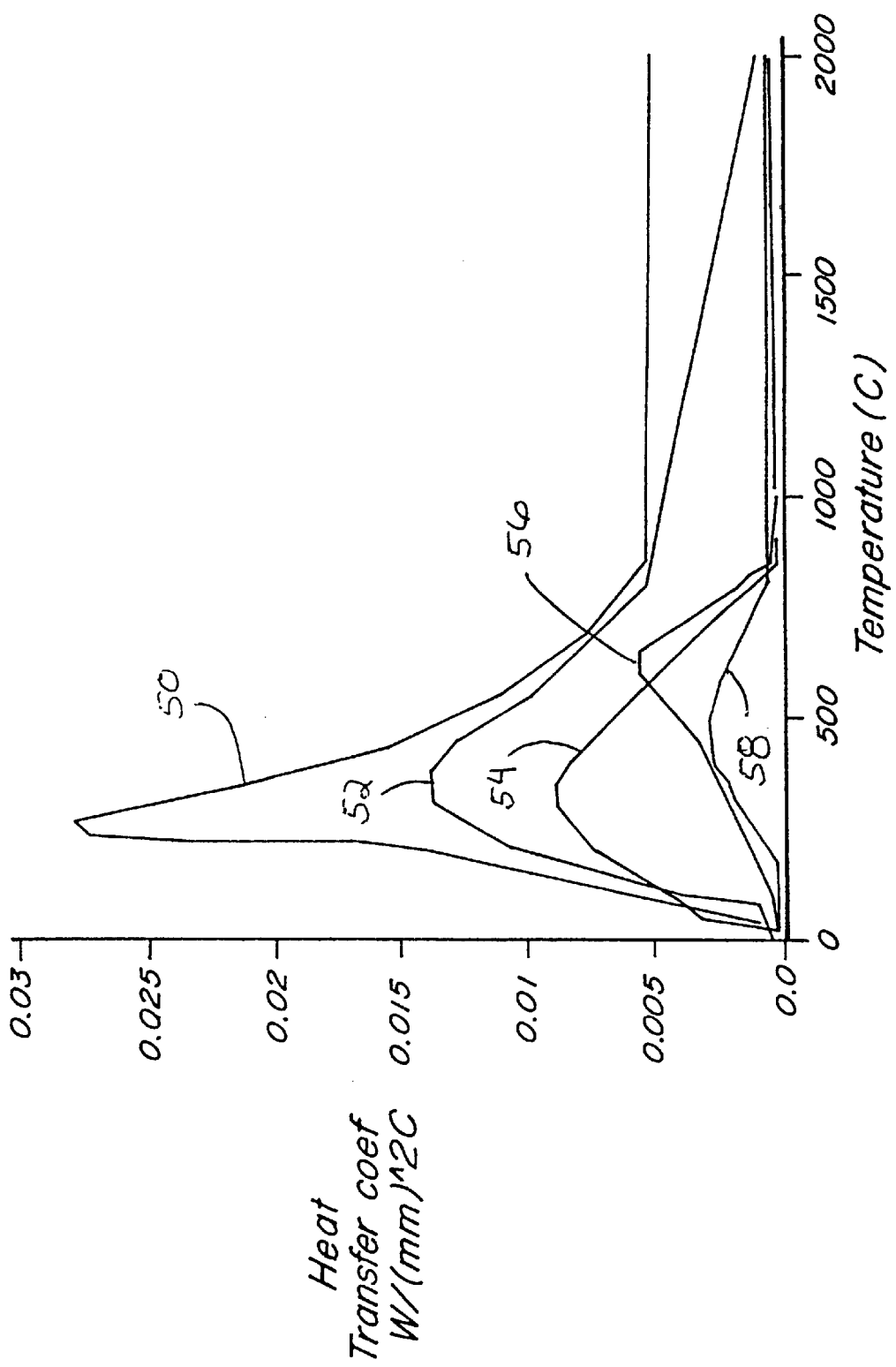
FIG. 5 is a graphical representation of heat transfer coefficients versus temperature for several representative quenches.

Referring to FIG. 5, initial heat transfer coefficient versus temperature curves for each of the five (5) quenches are shown. These curves were determined by placing thermocouples in two (2) different diameter cylindrical specimens of 304 stainless steel prepared for each quench, quenching the stainless steel specimens while measuring the rate of temperature decline over time, then calculating the heat transfer coefficients versus temperature using the equation of state discussed above. FIG. 5 includes a curve 50 for the highly agitated water quench; a curve 52 for the highly agitated oil quench; a curve 54 for the less agitated oil quench; a curve 56 for the hot oil quench; and a curve 58 for the high velocity air blast quench.

Once the hardness characteristics of the various specimens, 10, 20 and 40 have been collected after the quenches; the heat transfer coefficient versus temperature data determined; and correlating factors between the distinguishing characteristics of the respective specimens and the heat transfer coefficients determined, this information is stored in the storage device. Then, this information can be utilized for determining heat transfer coefficients versus temperature for other parts according to the method and apparatus of the present invention.

Figure 6:
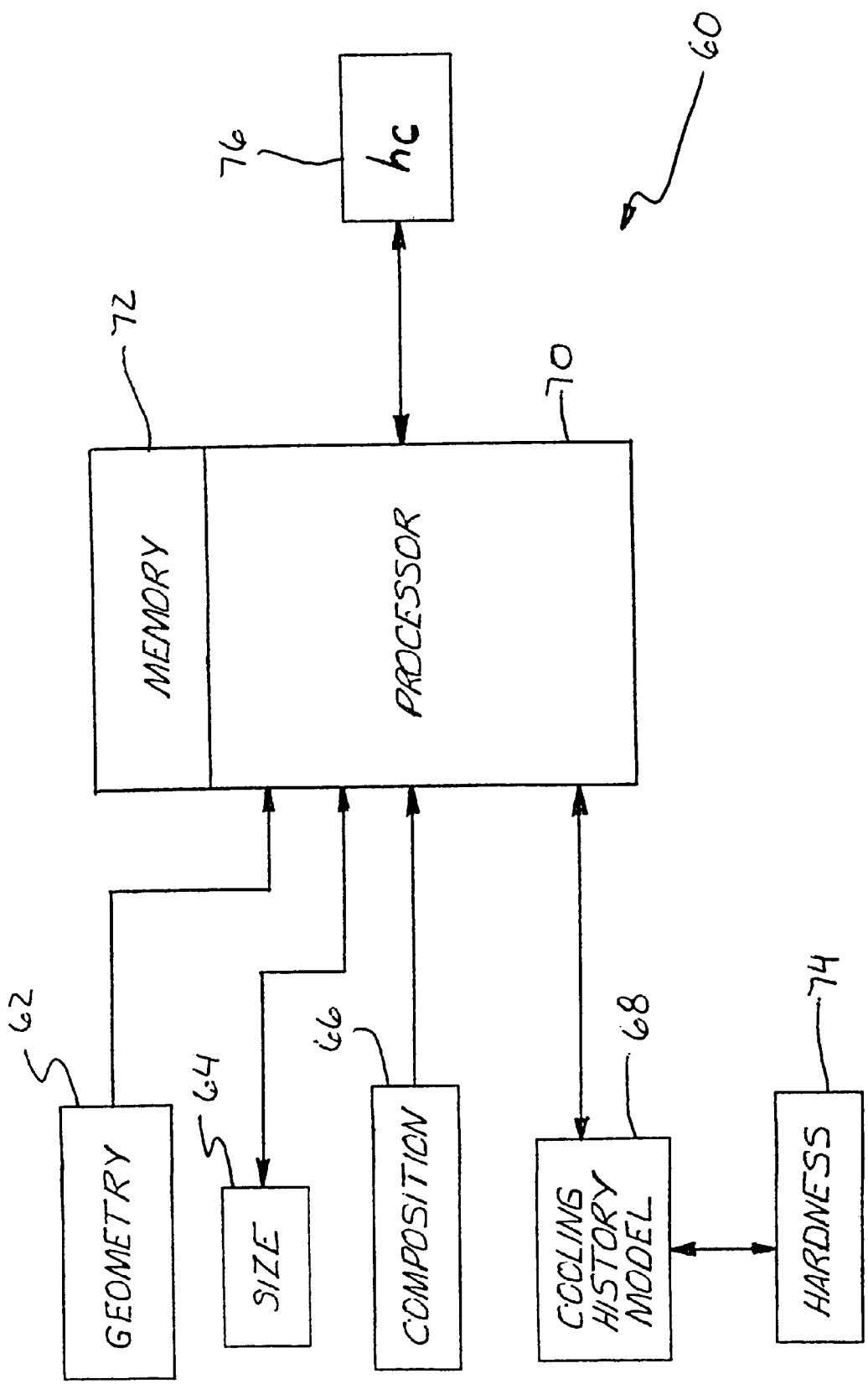
FIG. 6 is a flow diagram for the present invention.

Referring to FIG. 6, a flow diagram 60 illustrating the method and apparatus of the present invention is shown. Using the method and apparatus of the present invention, information representative of distinguishing characteristics of a subject steel part to be quenched, including, but not limited to, part geometry as shown at block 62, part size as shown at block 64, part composition as shown at block 66, and desired hardness characteristics of the part as represented by a cooling history model as shown at block 68 or a hardness traverse for the part as shown at block 74, are inputted into a computer processor 70. Processor 70 is operable for determining a difference between the information representative of the desired hardness characteristics and information representative of hardness characteristics produced by the known quenches on the specimen parts having at least one corresponding distinguishing characteristic, which latter information can be determined in the manner just described and is contained in a memory 72 associated with processor 70. If the difference is less than a predetermined value, indicating a matching specimen, the processor retrieves the heat transfer coefficient versus temperature data for the quench which produced the hardness characteristics, which is also stored in memory 72. The heat transfer coefficient versus temperature data can then be outputted as shown at block 76, using a suitable output device such as a printer or the like. On the other hand, if the difference is greater than or equal to the predetermined value, no matching specimen is considered to have been found. In this latter instance, processor 70 is operable to determine a new heat transfer coefficient versus temperature curve for producing the desired hardness characteristics, utilizing conventional algebraic interpolation techniques, based on the difference or differences between the desired hardness traverse and the closest stored hardness traverse or traverses for the specimen.

EXAMPLES

The following two (2) examples illustrate the collection of hardness data from two (2) specimens and characterizing an agitated water quench using the above described method and apparatus of the present invention. The agitated water quench of the specimens was conducted in a quench apparatus manufactured by Caterpillar Inc. using 5,000 gallons of water.

Example 1

A cylindrical test specimen of SAE 10B40 steel, 4.57 inches in diameter was austenized to 750° C. and then quenched. The initial temperature of the water quench was about 70° C. The entire specimen was quenched for about 120 to 180 seconds.

After the specimen was quenched it was sectioned and hardness measurements were taken on the sectional surface from the outer surface inward to the core using a Rockwell Indentations Hardness Test Machine. The results appear in Table 1 below.

TABLE 1

4.57 inch Cylinder Specimen of SAE 10B40

| Probe Depth (mm) | HRC (Hardness Rockwell C) |
|---|---|
| 0.23 | 58.6 |
| 0.46 | 57.7 |
| 0.69 | 57.2 |
| 0.91 | 56.7 |
| 1.14 | 56.5 |
| 1.37 | 56.4 |
| 1.60 | 56.4 |
| 1.83 | 56.3 |
| 2.06 | 56.1 |
| 2.29 | 55.9 |
| 2.51 | 55.7 |
| 2.74 | 55.7 |
| 2.97 | 55.6 |
| 3.20 | 55.5 |
| 3.43 | 55.7 |
| 3.66 | 55.9 |
| 3.89 | 55.6 |
| 4.11 | 55.5 |
| 4.34 | 55.4 |
| 4.57 | 55.5 |
| 4.80 | 55.6 |
| 5.03 | 55.3 |
| 5.26 | 54.8 |
| 5.49 | 54.8 |
| 5.72 | 54.7 |
| 5.94 | 54.7 |
| 6.17 | 54.5 |
| 6.40 | 54.6 |
| 6.63 | 54.0 |
| 6.86 | 54.2 |
| 7.09 | 53.5 |
| 7.32 | 52.1 |
| 7.54 | 52.5 |
| 7.77 | 50.5 |
| 8.00 | 49.9 |
| 8.23 | 49.3 |
| 8.46 | 46.0 |
| 8.69 | 44.1 |
| 8.92 | 42.2 |
| 9.14 | 40.3 |
| 9.37 | 38.8 |
| 9.60 | 37.0 |
| 9.83 | 34.9 |
| 10.06 | 33.6 |
| 10.29 | 32.6 |
| 10.52 | 31.9 |
| 10.74 | 30.5 |
| 10.97 | 30.5 |
| 11.20 | 29.5 |
| 11.43 | 28.8 |
| 11.66 | 28.7 |
| 11.89 | 28.3 |
| 12.12 | 27.6 |
| 12.34 | 27.7 |
| 12.57 | 27.6 |
| 12.80 | 27.7 |
| 13.03 | 27.6 |
| 13.26 | 28.0 |
| 13.49 | 27.4 |
| 13.72 | 26.9 |
| 13.94 | 26.7 |
| 14.17 | 27.0 |
| 14.40 | 26.5 |
| 14.63 | 25.7 |
| 14.86 | 14.6 |

As seen from Table 1, the hardness data was collected from the outer surface inward at increments of about 0.23 millimeters (mm). The hardness data from Table 1 was inputted into processor 70 along with the composition of the specimen, the size and shape of the specimen, and a series of temperature dependent heat transfer coefficients for the quench was produced according to the invention as explained above. The heat transfer coefficients are plotted versus temperature as curve 78 in FIG. 7.

Example 2

To illustrate the effect of specimen size on quench characterization, a second specimen which was a 3.23-inch diameter cylinder of the same material as the specimen in Example 1 was subjected to the same quench. The hardness results appear in Table 2 below.

TABLE 2

3.23 inch Cylinder Specimen of SAE 10B40

| Probe Depth (mm) | HRC (Hardness Rockwell C) |
|---|---|
| 0.23 | 57.2 |
| 0.46 | 58.8 |
| 0.69 | 58.9 |
| 0.91 | 58.6 |
| 1.14 | 58.4 |
| 1.37 | 58.2 |
| 1.60 | 58.0 |
| 1.83 | 57.9 |
| 2.06 | 57.6 |
| 2.29 | 57.3 |
| 2.51 | 57.2 |
| 2.74 | 57.1 |
| 2.97 | 56.9 |
| 3.20 | 56.4 |
| 3.43 | 56.4 |
| 3.66 | 56.3 |
| 3.89 | 56.2 |
| 4.11 | 56.5 |
| 4.34 | 56.3 |
| 4.57 | 56.1 |
| 4.80 | 55.8 |
| 5.03 | 56.0 |
| 5.26 | 55.8 |
| 5.49 | 55.9 |
| 5.72 | 55.9 |
| 5.94 | 55.6 |
| 6.17 | 55.9 |
| 6.40 | 55.3 |
| 6.63 | 55.4 |
| 6.86 | 55.4 |
| 7.09 | 55.6 |
| 7.32 | 55.3 |
| 7.54 | 55.7 |
| 7.77 | 55.3 |
| 8.00 | 55.5 |
| 8.23 | 55.5 |
| 8.46 | 55.2 |
| 8.69 | 54.9 |
| 8.92 | 54.7 |
| 9.14 | 53.4 |
| 9.37 | 53.1 |
| 9.60 | 53.0 |
| 9.83 | 53.4 |
| 10.06 | 51.9 |
| 10.29 | 50.3 |
| 10.52 | 49.6 |
| 10.74 | 50.9 |
| 10.97 | 48.6 |
| 11.20 | 47.7 |
| 11.43 | 45.5 |
| 11.66 | 43.0 |

Figure 8:
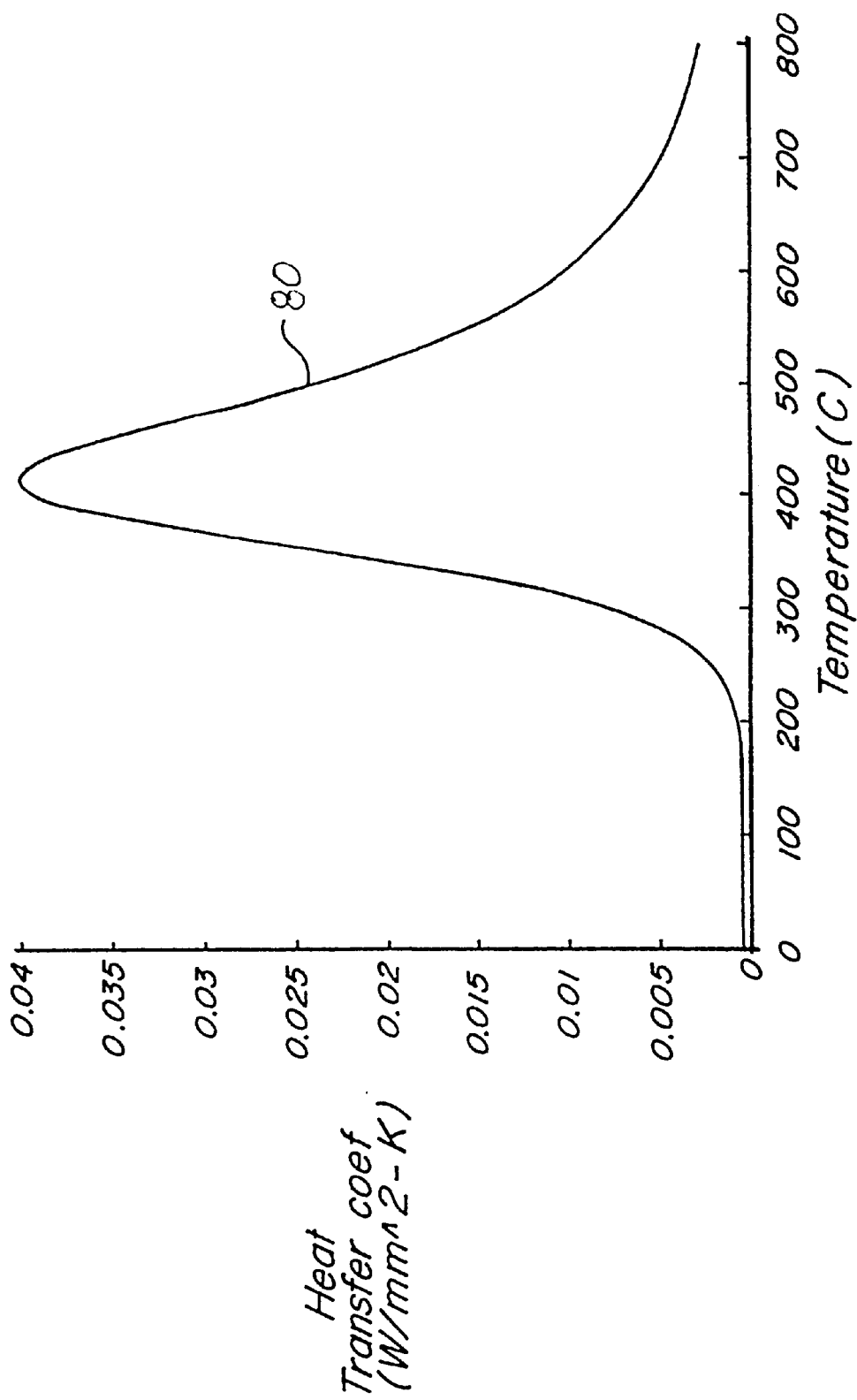

As in Example 1, this hardness data was collected and utilized to determine a series of heat transfer coefficients in the above-described manner. A heat transfer coefficient versus temperature curve 80 for the specimen is shown in FIG. 8.

Figure 7:
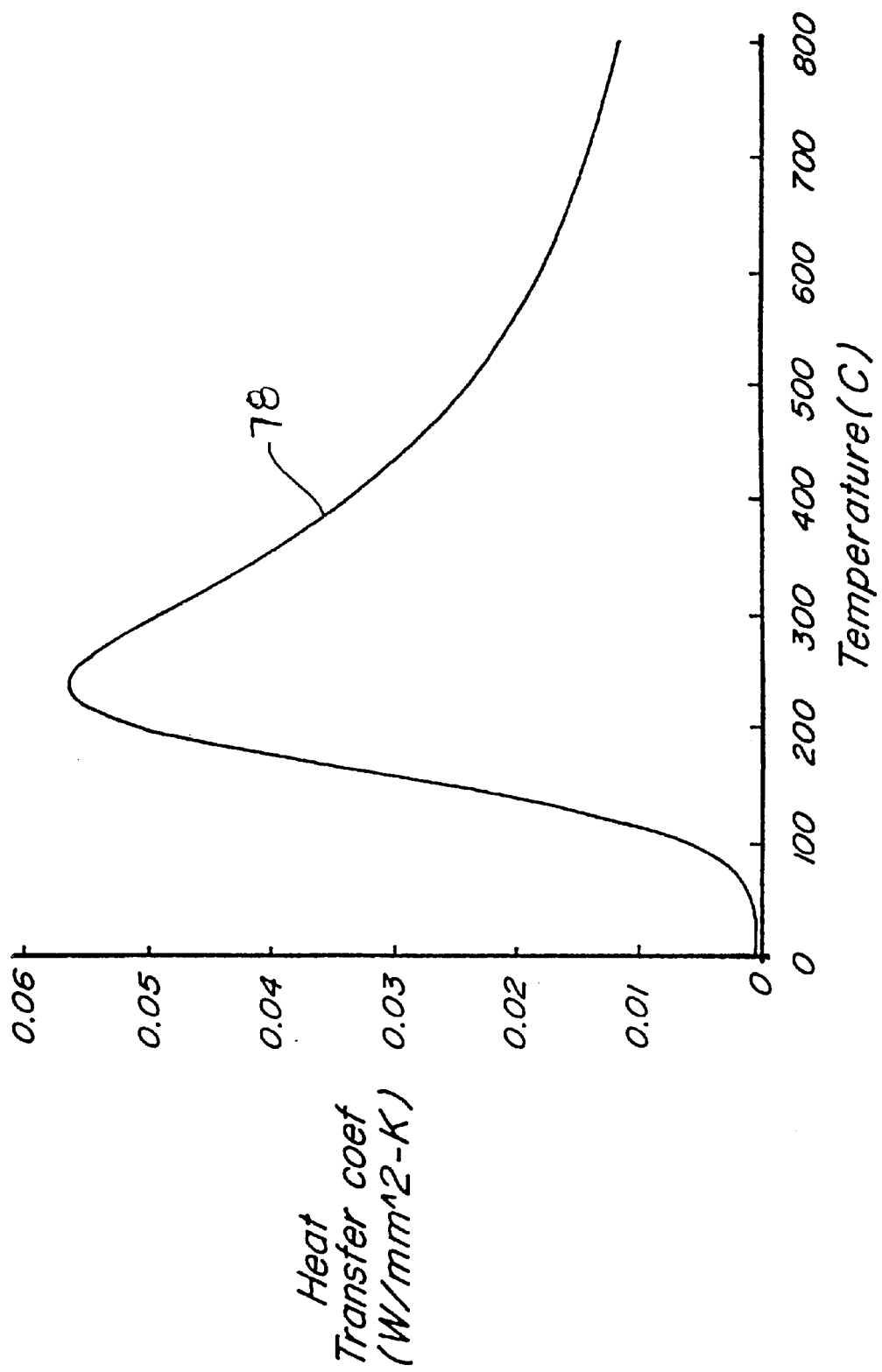
FIG. 7 is a graphical representation of heat transfer coefficients versus temperatures produced according to the present invention for a subject part; and, FIG. 8 is a graphical representation of heat transfer coefficients versus temperature produced according to the present invention for another subject part.

Comparison of the hardness data at corresponding distances from the outer surface of the specimens of Examples 1 and 2 indicates the important effect the size of the specimen, particularly the outer radius of curvature, has in determining the hardness at any given depth from the specimen surface. Importantly, this is reflected in the different temperature dependent heat transfer coefficient versus temperature curves 78 and 80 as shown in FIGS. 7 and 8. Curves 78 and 80 can then be used for determining heat transfer coefficient versus temperature curves for other parts or specimens using common algebraic interpolation techniques, based on differences between the other parts and the tested specimens. For instance, a heat transfer coefficient versus temperature curve for a 3.90 inch cylindrical diameter part of the same SAE 10B40 material would be determined to lie generally equidistant between curves 78 and 80 using a conventional algebraic interpolation technique.

Industrial Applicability

This invention relates to a method of characterizing a quench based on at least hardness measurements from steel specimens subject to the quench having at least one distinguishing property which affects the resulting hardness produced by the quench. The hardness measurements are used to determine a mathematical characterization of the quench which is a temperature dependent heat transfer coefficient curve. The curve can then be used to predict hardness in a wide variety of steel parts of different geometric characteristics, sizes and compositions.

Other aspects, objects and advantages of the present invention can be obtained from a study of the drawings, the disclosure and the appended claims.

What is claimed is:

1. A method for characterizing a quench for producing a desired hardness characteristic on a subject part, the subject part having at least one distinguishing characteristic affecting the hardness characteristic, the method comprising the step of:
   determining a difference between information representative of the desired hardness characteristic and information representative of a hardness characteristic produced by a known quench on at least one specimen having the at least one distinguishing characteristic, and;
   i. if the difference is less than a predetermined value, then producing information representative of a characterization of the known quench; and
   ii. if the difference is greater than or equal to the predetermined value, then determining and producing information representative of a characterization of a new quench based on the difference.

2. The method of claim 1 wherein the at least one distinguishing characteristic comprises a size characteristic.

3. The method of claim 1 wherein each of the characterizations of the quench comprises a series of heat transfer coefficients.

4. The method of claim 1 wherein the at least one distinguishing characteristic comprises a geometric characteristic.

5. The method of claim 1 wherein said geometric characteristic is a shape selected from the group consisting of a cylindrical shape, a rectangular shape and a tubular shape.

6. The method of claim 1 wherein the determination of the characterization of the new quench comprises interpolation of the information representative of the hardness characteristic produced by the known quench.

7. The method of claim 1 wherein the at least one distinguishing characteristic comprises composition.

8. The method of claim 7 wherein said composition comprises a low hardenability steel.

9. The method of claim 7 wherein said composition comprises a high hardenability steel.

10. The method of claim 7 wherein said composition comprises a medium hardenability steel.

11. The method of claim 1 wherein the at least one distinguishing characteristic comprises information generally corresponding to a cooling history for elements of the part or specimen.

12. Apparatus for characterizing a quench for producing a desired hardness characteristic on a subject part, the subject part having at least one distinguishing characteristic affecting the hardness characteristic, the apparatus comprising:
   a storage device containing information representative of a hardness characteristic produced by at least one known quench on at least one specimen, information representative of at least one distinguishing characteristic of the at least one specimen affecting the hardness characteristic thereof, and information representative of a characterization of the at least one known quench;
   a processor operable for determining a difference between information representative of the desired hardness characteristic and the stored information representative of the hardness characteristic produced by the known quench on the at least one specimen, and;
   i. if the difference is less than a predetermined value, then retrieving the stored information representative of the characterization of the known quench, and;
   ii. if the difference is greater than or equal to the predetermined value, then determining information representative of a characterization of a new quench based on the difference.

13. Apparatus for characterizing a quench of claim 12 wherein the at least one known quench comprises a highly agitated water quench; a highly agitated oil quench; a less agitated oil quench; a hot oil quench; and a high viscosity air blast quench.

14. Apparatus for characterizing a quench of claim 12 further comprising an output device operable for outputting the information representative of the characterizations of the quenches.

15. Apparatus for characterizing a quench of claim 12 wherein the information representative of the characterizations of the quenches comprises heat transfer coefficient data.

* * * * *